(12) United States Patent
Wibaux et al.

(10) Patent No.: US 12,076,216 B2
(45) Date of Patent: Sep. 3, 2024

(54) WOUND DRESSING (71) Applicant: SCAPA UK LIMITED, Greater Manchester (GB)

(72) Inventors: Anne Wibaux, Greater Manchester (GB); Katerina Prokopiou, Greater Manchester (GB)

(73) Assignee: SCAPA UK LIMITED, Greater Manchester (GB)

( * ) Notice: Subject to any disclaimer, the term of this patent is extended or adjusted under 35 U.S.C. 154(b) by 0 days.

(21) Appl. No.: 18/156,551

(22) Filed: Jan. 19, 2023

(65) Prior Publication Data

US 2023/0149221 A1    May 18, 2023

Related U.S. Application Data (63) Continuation of application No. 16/641,004, filed as application No. PCT/GB2018/052394 on Aug. 23, 2018, now abandoned.

(30) Foreign Application Priority Data

Aug. 23, 2017  (GB) ...................................... 1713511

(51) Int. Cl.
*A61F 13/0203*   (2024.01)
*A61F 13/02*     (2024.01)
(Continued)

(52) U.S. Cl.
CPC ...... *A61F 13/0223* (2013.01); *A61F 13/0209* (2013.01); *A61F 13/0213* (2013.01);
(Continued)

(58) Field of Classification Search
CPC .............. A61F 13/0223; A61F 13/0209; A61F 13/0213; A61F 13/0276; A61F 13/00; A61F 13/02; A61F 13/00008; A61F 13/00021; A61F 13/0203; A61F 13/0266; A61F 2013/00089; A61F 2013/00259; A61F 2013/00246; A61F 2013/00582;
(Continued)

(56) References Cited

U.S. PATENT DOCUMENTS 4,063,452 A   12/1977  Bradshaw
4,181,127 A    1/1980  Linsky et al.
(Continued)

FOREIGN PATENT DOCUMENTS

CN    204246325 U    4/2015
EP      0424165 A1   4/1991
(Continued)

OTHER PUBLICATIONS

BASF.pdf: "Thermoplastic Polyurethane Elastomers (TPU) Elastollan—Material Properties"; Aug. 2019 (Year: 2019).*
(Continued)

*Primary Examiner* — Caitlin A Carreiro
(74) *Attorney, Agent, or Firm* — Farber LLC (57) ABSTRACT

A wound dressing containing a breathable film, a transparent fluid-absorption layer, and a transparent fluid-wicking layer is described. The wound dressing may be used for treating or preventing wounds and/or for securement of a device that has been at least partially inserted in the skin.

17 Claims, 3 Drawing Sheets

(51) Int. Cl.
*A61F 13/0206* (2024.01)
*A61M 25/02* (2006.01)

(52) U.S. Cl.
CPC ......... *A61F 13/0276* (2013.01); *A61M 25/02* (2013.01); *A61M 2025/0253* (2013.01)

(58) Field of Classification Search
CPC .......... A61M 25/02; A61M 2025/0253; A61M 35/00; A61K 9/70; A61L 15/00; A61L 26/00
USPC .......... 602/41–44, 52, 56, 58, 904; 424/445; 604/304
See application file for complete search history.

(56) References Cited

U.S. PATENT DOCUMENTS

| | | | |
|---|---|---|---|
| 4,753,231 A * | 6/1988 | Lang .................. | A61L 15/58 602/44 |
| 4,920,158 A | 4/1990 | Murray et al. | |
| 4,928,680 A | 5/1990 | Sandbank | |
| 5,064,652 A | 11/1991 | Bay | |
| 5,160,328 A | 11/1992 | Cartmell et al. | |
| 5,183,664 A | 2/1993 | Ansell | |
| 1,909,244 A | 7/1994 | Quarfoot et al. | |
| 5,336,209 A | 8/1994 | Porzilli | |
| 5,480,377 A | 1/1996 | Cartmell et al. | |
| 5,593,395 A | 1/1997 | Martz | |
| 5,622,711 A | 4/1997 | Chen | |
| 5,633,010 A | 5/1997 | Chen | |
| 5,733,570 A | 3/1998 | Chen et al. | |
| 5,910,125 A | 6/1999 | Cummings et al. | |
| 5,994,613 A | 11/1999 | Cummings et al. | |
| 6,075,177 A | 6/2000 | Bahia et al. | |
| 6,096,942 A | 8/2000 | Hack | |
| 6,124,520 A * | 9/2000 | Roberts ............... | A61F 13/0206 602/56 |
| 6,124,521 A | 9/2000 | Roberts | |
| 6,482,192 B2 | 11/2002 | Haarer et al. | |
| 6,566,575 B1 | 5/2003 | Stickels et al. | |
| 6,573,419 B2 | 6/2003 | Naimer | |
| 6,596,402 B2 | 7/2003 | Soerens et al. | |
| 6,838,589 B2 | 1/2005 | Liedtke et al. | |
| 6,903,243 B1 | 6/2005 | Burton | |
| 6,998,511 B2 | 2/2006 | Worthley | |
| 7,005,143 B2 | 2/2006 | Abuelyaman et al. | |
| 7,008,979 B2 | 3/2006 | Schottman et al. | |
| 7,030,288 B2 | 4/2006 | Liedtke et al. | |
| 7,276,247 B2 | 10/2007 | Fansler et al. | |
| 7,342,047 B2 | 3/2008 | Lewandowski et al. | |
| 7,563,940 B2 | 7/2009 | Kurata | |
| 7,569,742 B2 | 8/2009 | Haggstrom et al. | |
| 7,576,256 B2 | 8/2009 | Bjornberg et al. | |
| 7,858,838 B2 | 12/2010 | Holm et al. | |
| 7,993,670 B2 | 8/2011 | Simonson et al. | |
| 8,080,702 B2 | 12/2011 | Blott et al. | |
| 8,425,996 B2 | 4/2013 | Gorski et al. | |
| 8,444,612 B2 | 5/2013 | Patel et al. | |
| 8,486,004 B1 | 7/2013 | Propp | |
| 8,609,131 B2 | 12/2013 | Plaut et al. | |
| 8,784,773 B2 | 7/2014 | Mojmeli et al. | |
| 8,829,263 B2 | 9/2014 | Haggstrom et al. | |
| 9,061,095 B2 * | 6/2015 | Adie .................. | A61F 13/00068 |
| 9,132,040 B2 | 9/2015 | Van Holten et al. | |
| 9,566,417 B1 | 2/2017 | Propp | |
| 2001/0016985 A1 | 8/2001 | Insley et al. | |
| 2001/0018602 A1 | 8/2001 | Augustine et al. | |
| 2002/0052570 A1 | 5/2002 | Naimer | |
| 2002/0111576 A1 * | 8/2002 | Greene ................ | A61L 15/64 602/42 |
| 2002/0115975 A1 | 8/2002 | Haarer et al. | |
| 2002/0132540 A1 | 9/2002 | Soerens et al. | |
| 2002/0169405 A1 | 11/2002 | Roberts | |
| 2002/0183676 A1 | 12/2002 | Augustine | |
| 2003/0028162 A1 | 2/2003 | Haarer et al. | |
| 2003/0114818 A1 | 6/2003 | Benecke et al. | |
| 2003/0125680 A1 | 7/2003 | Ding | |
| 2003/0175333 A1 | 9/2003 | Shefer et al. | |
| 2003/0203011 A1 | 10/2003 | Abuelyaman et al. | |
| 2003/0203991 A1 | 10/2003 | Schottman et al. | |
| 2004/0127614 A1 | 7/2004 | Jiang et al. | |
| 2004/0162512 A1 | 8/2004 | Liedtke et al. | |
| 2004/0220505 A1 | 11/2004 | Worthley | |
| 2005/0113733 A1 | 5/2005 | Liedtke et al. | |
| 2005/0192370 A1 | 9/2005 | Fansler et al. | |
| 2005/0194559 A1 | 9/2005 | Lewandowski et al. | |
| 2006/0039982 A1 | 2/2006 | Abuelyaman et al. | |
| 2006/0094997 A1 | 5/2006 | Kurata | |
| 2006/0129080 A1 | 6/2006 | Bjornberg et al. | |
| 2006/0165762 A1 | 7/2006 | Plaut et al. | |
| 2006/0165999 A1 | 7/2006 | Fansler et al. | |
| 2006/0182787 A1 | 8/2006 | Jaenichen et al. | |
| 2007/0078366 A1 | 4/2007 | Haggstrom et al. | |
| 2007/0154529 A1 | 7/2007 | Bullerdiek | |
| 2007/0161937 A1 | 7/2007 | Aali | |
| 2008/0039759 A1 | 2/2008 | Holm et al. | |
| 2008/0091233 A1 | 4/2008 | Ellis-Behnke et al. | |
| 2009/0227935 A1 | 9/2009 | Zanella et al. | |
| 2010/0179463 A1 | 7/2010 | Greener et al. | |
| 2010/0196636 A1 | 8/2010 | Gorski et al. | |
| 2010/0298793 A1 | 11/2010 | Blott et al. | |
| 2010/0331797 A1 | 12/2010 | Patel et al. | |
| 2011/0087179 A2 | 4/2011 | Blott et al. | |
| 2011/0112457 A1 * | 5/2011 | Holm .................. | A61F 13/0226 428/355 R |
| 2011/0189287 A1 | 8/2011 | Abbott et al. | |
| 2012/0136323 A1 | 5/2012 | Stasko et al. | |
| 2013/0131621 A1 | 5/2013 | Van Holten et al. | |
| 2013/0138060 A1 | 5/2013 | Haggstrom et al. | |
| 2013/0165821 A1 | 6/2013 | Freedman et al. | |
| 2013/0224256 A1 | 8/2013 | Mojmeli Renani et al. | |
| 2013/0243847 A1 | 9/2013 | McDonald et al. | |
| 2013/0331822 A1 | 12/2013 | Patel et al. | |
| 2014/0121649 A1 | 5/2014 | Calco | |
| 2015/0065965 A1 | 3/2015 | Haggstrom et al. | |
| 2015/0157251 A1 | 6/2015 | Nelson | |
| 2015/0209198 A1 | 7/2015 | Aizenberg et al. | |
| 2015/0342787 A1 | 12/2015 | Haisley | |
| 2016/0000609 A1 | 1/2016 | Van Holten et al. | |
| 2016/0015570 A1 | 1/2016 | Heinecke et al. | |
| 2016/0143786 A1 | 5/2016 | Bjork et al. | |
| 2016/0215324 A1 | 7/2016 | Srinivasan et al. | |
| 2016/0339158 A1 | 11/2016 | Collinson et al. | |

FOREIGN PATENT DOCUMENTS

| | | | | |
|---|---|---|---|---|
| EP | 1900348 A1 | 3/2008 | | |
| EP | 2572737 A1 | 3/2013 | | |
| GB | 2537841 A * | 11/2016 | ....... | A61F 13/00029 |
| WO | 9304691 A1 | 3/1993 | | |
| WO | 9310795 A1 | 6/1993 | | |
| WO | 9707758 A1 | 3/1997 | | |
| WO | 9724149 A1 | 7/1997 | | |
| WO | 9734947 A1 | 9/1997 | | |
| WO | 9802270 A1 | 1/1998 | | |
| WO | 0006214 A1 | 2/2000 | | |
| WO | 0006215 A1 | 2/2000 | | |
| WO | 0007638 A1 | 2/2000 | | |
| WO | 0048319 A1 | 8/2000 | | |
| WO | 0065143 A1 | 11/2000 | | |
| WO | 0196422 A1 | 12/2001 | | |
| WO | 2005079718 A1 | 9/2005 | | |
| WO | 2011008360 A1 | 1/2011 | | |
| WO | 2011104388 A1 | 9/2011 | | |
| WO | 2015173546 A1 | 11/2015 | | |

OTHER PUBLICATIONS

BASF Thermoplastic Polyurethane Elastomers (TPU) Elastollan—Material Properties (BASF.pdf) (Year: 2019).*
Austin, A. et al. "A Microbiological Study of Bioxzyme™—A Revolutionary New Active Wound Dressing Technology," 2003, available at www.wounds-uk.com/posterabstracfs2003.pdf (1 page).

(56) References Cited

OTHER PUBLICATIONS

Matthews, R., "Honey Holds Key to Killing off Ward Superbug," The Telegraph, Jan. 26, 2003 (2 pages).
International Search Report for PCT/GB2018/052394 dated Nov. 13, 2018 (3 pages).
BASF Thermoplastic Polyurethane Elastomers (TPU) Elastollan—Material Properties (BASF.pdf) dated 2019 (28 pages).

* cited by examiner

WOUND DRESSING

CROSS-REFERENCE TO RELATED APPLICATIONS

This application is a continuation of U.S. application Ser. No. 16/641,004, filed on Feb. 21, 2020, which is the U.S. national stage entry under 35 U.S.C. § 371 of International Application No. PCT/GB2018/052394, filed on Aug. 23, 2018, incorporated by reference herein in its entirety, PCT/GB2018/052394 claiming the benefit of priority to GB 1713511.2, filed on Aug. 23, 2017.

TECHNICAL FIELD

The present invention relates generally to wound dressings, including wound dressings that allow the wound to be observed, for example by a medical practitioner. The present invention further relates to the various uses of said wound dressings for treating or preventing a wound and for securement of a device that has been at least partially Inserted through the skin of a patient. The present invention also relates to methods of making said wound dressings.

BACKGROUND

The production of exudate or fluid from a mammalian wound is important for wound healing. Exudate is an acidic solution containing mainly water, but may also contain electrolytes, nutrients, proteins, inflammatory mediators, protein digesting enzymes, growth factors and various types of ceil (e.g. white blood cells). Whilst wound healing generally benefits from a moist environment, too much exudate may delay healing and deplete patient quality of life.

Wound dressings may be designed to assist in maintaining a moist wound environment and/or managing exudate accumulation in the wound and pen-wound area. For example, wound dressings may be designed to absorb excess wound exudate and/or allow transmission of water vapour through the dressing. A medical practitioner may be required to check the progression of wound healing and decide when the wound dressing should be changed (e.g. when it is saturated). However, this is often difficult to judge since the wound dressing may need to be removed completely to judge the progression of wound healing, it is therefore desirable to provide alternative and/or improved wound dressings that provide an advantageous balance of the factors that contribute to wound healing.

SUMMARY

In accordance with a first aspect of the present invention there is provided a wound dressing comprising:
a breathable film;
a fluid-absorption layer; and
a fluid-wicking layer for directing fluid towards the absorbent layer;
wherein the fluid-absorption layer has a saline absorption capacity of at least about 50 wt % based on the weight of the fluid-absorption layer;
wherein the fluid-absorption layer is positioned laterally to the fluid-wicking layer and breathable film.

In accordance with a second aspect of the present invention there is provided a wound dressing according to any aspect or embodiment of the present invention for use in treating or preventing a wound.

In accordance with a third aspect of the present invention there is provided a wound dressing according to any aspect or embodiment of the present invention for use in securement of a device that has been at least partially inserted through the skin.

In accordance with a fourth aspect of the present invention there is provided a method of treating or preventing a wound, the method comprising applying a wound dressing according to any aspect or embodiment of the present invention to the wound.

In accordance with a fifth aspect of the present Invention there is provided a method of securing a device that has been at least partially inserted through the skin of a subject, the method comprising applying a wound dressing according to any aspect or embodiment of the present invention to the skin where the device has been at least partially inserted.

In accordance with a sixth aspect of the present Invention there is provided a method of making a wound dressing according to any aspect or embodiment of the present invention, the method comprising providing a breathable film, a fluid-absorption layer, a fluid-wicking layer, optionally one or more adhesive layers and optionally a non-absorbent waterproof layer and adhering the layers to each other to form a multilayer structure.

In certain embodiments, the breathable film is transparent. Alternatively or additionally, in certain embodiments the fluid-wicking layer is transparent. Further alternatively or additionally, in certain embodiments at least part of the wound dressing is transparent and the transparent part of the wound dressing enables observation of the wound.

In certain embodiments, the fluid-absorption layer is positioned between the breathable film and the fluid-wicking layer. The breathable film may be positioned on the outer-facing side of the wound dressing. The fluid-wicking layer may be positioned on the wound-facing side of the wound dressing.

In certain embodiments, the wound dressing further comprises one or more adhesive layers. The one or more adhesive layers may, for example, be positioned between the breathable film and the fluid-absorption layer and/or between the fluid-absorption layer and the fluid-wicking layer.

In certain embodiments, the wound dressing further comprises a non-absorbent waterproof layer. The non-absorbent waterproof layer may, for example, be positioned on the wound-facing side of the wound dressing, for example the wound-facing side of the fluid-wicking layer.

Certain embodiments of any aspect of the present invention may provide one or more of the following advantages:
High (e.g. improved) absorption of wound exudate;
High (e.g. improved) breathability to enable transmission of water vapour through the wound dressing;
Hold wound exudate m a location away from the wound or peri-wound area;
Transparent to enable observation of the wound;
Reduce number of unnecessary wound dressing changes,
Reduce risk of infection;
Maintain some moisture in wound area.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

BRIEF DESCRIPTION OF THE FIGURES

FIGS. 6 and 7 depict embodiments of wound dressings of the present invention as viewed from above.

The layers of the wound dressings are shown as follows;
A: Breathable film;
B: Adhesive layer;
C: Fluid-absorption layer;
D: Fluid-wicking layer;
E: Non-absorbent waterproof layer
F: Liner
X: A transparent part of the wound dressing
Y: Fluid-absorption layer

DETAILED DESCRIPTION

There is provided herein a wound dressing that enables high absorption of wound exudate and/or high transmission of water vapour therethrough. The wound dressing comprises a breathable film, a fluid-wicking layer and a fluid-absorption layer. The fluid-absorption layer may be positioned laterally to the breathable film and/or fluid-wicking layer.

There is also provided herein a wound dressing that is at least partially transparent, thus enabling observation of the wound. The transparent wound dressing may compose a transparent breathable film, a transparent fluid-wicking layer and a fluid-absorption layer. The fluid-absorption layer may be positioned laterally to the transparent breathable film and/or transparent fluid-wicking layer. This may provide an area of the wound dressing that is transparent and enables observation of the wound.

At least a part of the wound dressing is "Transparent" in that the wound is visible through the transparent part of the wound dressing. "Transparent" as used herein means that the material transmits incident light with negligible scattering and little absorption, enabling the wound to be seen through the transparent part under typical unaided viewing conditions. This may, for example, be judged by whether the words of size 12 text in Times New Roman font printing on white paper can be read through the transparent part of the wound dressing.

This may, for example, be judged by refractive index. For example, the transparent part of the wound dressing may have a refractive index ranging from about 1 to about 2. For example the refractive index may be equal to or less than about 1.3 or equal to or less than about 1.8 or equal to or less than about 1.7. The refractive index may be measured using a refractometer.

Alternatively or additionally, this may be judged by % light transmission, for example using a transparency meter A transparent part of the wound dressing may have a total transmittance of at least about 50% or at least about 55% or at least about 60% or at least about 65% or at least about 70% or at least about 80% or at least about 85% or at least about 90%.

The transparent part of the wound dressing may, for example, have a surface area that is at least about 10% of the total surface area of the wound dressing. For example, the transparent part of the wound dressing may have a surface area that is at least about 15% or at least about 20% or at least about 25% or at least about 30% or at least about 35% or at least about 40% or at least about 45% or at least about 50% of the total surface area of the wound dressing.

The transparent part of the wound dressing may, for example, have a surface area that is equal to or less than about 90% of the total surface area of the wound dressing. For example, the transparent part of the wound dressing may have a surface area that is equal to or less than about 85% or equal to or less than about 80% or equal to or less than about 75% or equal to or less than about 70% or equal to or less than about 65% or equal to or less than about 60% of the total surface area of the wound dressing.

The transparent part of the wound dressing may, for example, relate to a part of the wound dressing in which the absorbent layer is not present. For example, the transparent part of the wound dressing may comprise only of (consist of) the transparent part of breathable film and the transparent part of fluid-wicking layer. A laminate comprising both the transparent breathable film and the transparent fluid-wicking layer may itself be transparent.

The fluid-absorption layer may, for example, be positioned between the breathable film and the fluid-wicking layer. The breathable film may, for example, be positioned on an outer-facing side of the fluid-absorption layer and/or wound dressing. By "outer-facing side", it is meant the side or face of the wound dressing or fluid-absorption layer that is most distant from the wound when the wound dressing is in use. The breathable film may be the outermost layer of the wound dressing. The fluid-wicking layer may, for example, be positioned on a wound-facing side of the fluid-absorption layer and/or wound dressing. By "wound-facing side", it is meant the side or face of the wound dressing or fluid-absorption layer that is closes to the wound when the wound dressing is in use.

The wound dressing may, for example, further comprise one or more adhesive layers. The one or more adhesive layers may be used to adhere the various layers of the wound dressing together. For example, the wound dressing may comprise an adhesive layer between the breathable film and the fluid-absorption layer. This adhesive layer may, for example, be breathable. Alternatively or additionally, the wound dressing may comprise an adhesive layer between the fluid-wicking layer and the fluid-absorption layer.

The wound dressing may, for example, further comprise a non-absorbent waterproof layer on the wound-facing side of the fluid-absorption layer.

The wound dressing may, for example, further comprise one or more liners on the wound-facing side of the fluid-absorption layer and/or fluid-wicking layer. The liner(s) are intended to be removed prior to application of the wound dressing to the wound.

Breathable Film

The breathable film acts as a barrier to protect the wound from the external environment. For example, the breathable film acts as a barrier to viruses and bacteria to prevent wound infection.

The breathable film is "breathable" in that it does not allow transmission of liquids (e.g. water) but does allow transmission of gases (e.g. water vapour) through the film.

For example, the breathable film may have a moisture vapour transmission rate (MVTR) equal to or greater than about 400 g/m$^2$/24 hours. For example, the breathable film may have a MVTR equal to or greater than about 450 g/m$^2$/24 hours or equal to or greater than about 500 g/m$^2$/24 hours or equal to or greater than about 550 g/m$^2$/24 hours or equal to or greater than about 600 g/m$^2$/24 hours or equal to or greater than about 650 g/m²/24 hours or equal to or greater than about 700 g/m²/24 hours or equal to or greater than about 750 g/m²/24 hours or equal to or greater than about 800 g/m²/24 hours or equal to or greater than about 650 g/m²/24 hours or equal to or greater than about 900 g/m²/24 hours or equal to or greater than about 950 g/m²/24 hours or equal to or greater than about 1000 g/m²/24 hours.

For example, the breathable film may have a MVTR equal to or less than about 3000 g/m²/24 hours. For example, the breathable film may have a MVTR equal to or less than about 2800 g/m²/24 hours or equal to or less than about 2600 g/m²/24 hours or equal to or less than about 2500 g/m²/24 hours or equal to or less than about 2400 g/m²/24 hours or equal to or less than about 2200 g/m²/24 hours or equal to or less than about 2000 g/m²/24 hours or equal to or less than about 1800 g/m²/24 hours or equal to or less than about 1600 g/m²/24 hours or equal to or less than about 1500 g/m²/24 hours.

The whole or a part of the breathable film may be "transparent" as defined above The breathable film may, for example, comprise one or more layers, for example one or more polymeric layers. The one or more layers may, for example, be adhered together using an adhesive composition.

The polymeric layers of the breathable film may, for example, comprise any suitable polymer For example, the polymeric layers of the breathable film may comprise one or more of polyolefins (e.g. polyethylene), polyesters, polyurethanes, polystyrene, carboxymethyl cellulose and copolymers and mixtures thereof.

For example, the breathable film may comprise or consist of a polyurethane film layer.

One or more layers of the breathable film may be adhesive in that they are able to adhere to the adjacent layer in the wound dressing and/or adhere to the skin of a patient. If the layer of the breathable film that is adjacent to the next layer in the wound dressing and/or adjacent to the skin is not adhesive, an additional adhesive layer may be required to hold the layers of the wound dressing together and/or hold the breathable film to the skin.

The breathable film may, for example, have a thickness of at least about 5 μm. For example, the breathable film may have a thickness of at least about 10 μm or at least about 15 μm. The breathable film may have a thickness equal to or less than about 300 μm. For example, the breathable film may have a thickness equal to or less than about 250 μm or equal to or less than about 200 μm or equal to or less than about 150 μm or equal to or less than about 100 μm or equal to or less than about 50 μm. For example, the breathable film may have a thickness ranging from about 5 μm to about 300 μm or from about 10 μm to about 200 μm or from about 15 μm to about 50 μm.

The breathable film may, for example, cover at least about 90% of the surface area of the wound dressing. For example, the breathable film may cover at least about 92% or at least about 94% or at least about 95% or at least about 96% or at least about 98% or at least about 99% or about 100% of the surface area of the film. Preferably, the breathable film covers 100% of the surface area of the fluid-absorption layer. This is to prevent leaking of wound exudate from the wound or wound dressing to the external environment.

Preferably, the breathable film is located on the outer-facing side of the fluid-absorption layer and wound dressing. Preferably, the breathable film is the outermost layer of the wound dressing.

Fluid-Absorption Layer

The fluid-absorption layer acts to absorb wound exudate to prevent it accumulating in the wound. The fluid-absorption layer is preferably located on the wound-facing side of the breathable film. The fluid-absorption layer may be located on the outer-facing side of the fluid-wicking layer.

Preferably, the fluid-absorption layer is positioned such that it does not overlay the wound or peri-wound area of the wound when the wound dressing is in use. This may prevent the would exudate from being in contact with the wound or peri-wound area, thus preventing damage or delay of healing due to the toxic and acidic nature of the wound exudate. Alternatively or additionally, when the fluid-absorption layer is not transparent, it does not prevent observation of the wound and/or peri-wound area through a transparent part of the wound dressing (e.g. transparent breathable film and/or transparent fluid-wicking layer).

The fluid-absorption layer may therefore be positioned laterally to the fluid-wicking layer and/or breathable film. This means that the fluid-absorption layer does not completely cover the surface area of the fluid-wicking layer and/or breathable film. The lateral position of the fluid-absorption layer may be central or at the periphery of the total surface area of the wound dressing.

However, one or both the fluid-wicking layer and breathable film may partially or completely overlay the fluid-absorption layer. One or both of the fluid-wicking layer and breathable film may have surface area that is larger than the surface are of the fluid-absorption layer.

The fluid-absorption layer may, for example, have a surface area equal to or less than about 90% of the total surface area of the wound dressing. For example, the fluid-absorption layer may have a surface area equal to or less than about 85% or equal to or less than about 80% or equal to or less than about 75% or equal to or less than about 70% or equal to or less than about 65% or equal to or less than about 60% or equal to or less than about 55% or equal to or less than about 50% of the total surface area of the wound dressing.

The fluid-absorption layer may, for example, have a surface area of at least about 5% of the total surface area of the wound dressing. For example, the fluid-absorption layer may have a surface area of at least about 10% or at least about 15% or at least about 20% or at least about 25% of the total surface area of the wound dressing.

The fluid-absorption layer may, for example, positioned in the peripheral area of the wound dressing. By peripheral, it is meant that the fluid-absorption layer is located at one or more edges of the wound dressing and not in the central area of the wound dressing. The peripheral or edges of the wound dressing may, for example, be defined as the outermost 50% of the surface area of the wound dressing.

A transparent part of the wound dressing may, for example, be located at the centre of the wound dressing. In use, the transparent part of the wound dressing may be positioned over the wound, such that the wound may be located at the centre of wound dressing in use.

Figure 6:
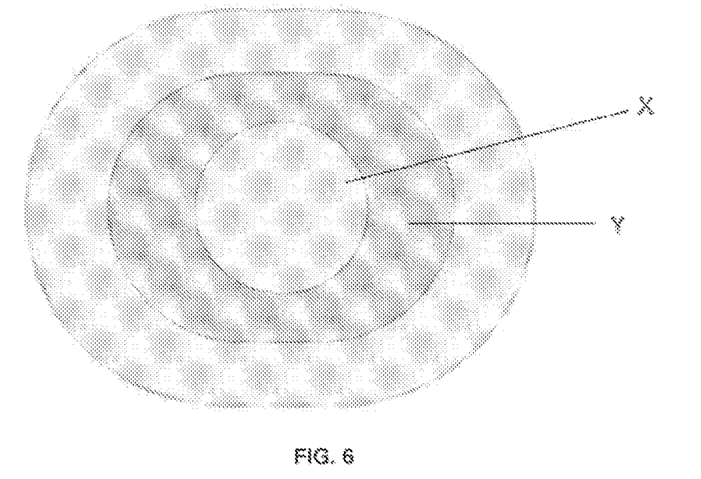

The fluid-absorption layer may, for example, be a continuous layer. By "continuous" it is meant that the fluid-absorption layer is formed from a single portion. The continuous layer may, for example, be any suitable shape including, for example, square, rectangular, circular oval, polygonal, or irregular shaped. The continuous layer may, for example, be annular (ring-shaped) comprising an opening that is completely surround by the fluid-absorption layer. The perimeter of the annular fluid-absorption may, for example, be any suitable shape including, for example, square, rectangular, circular, oval, polygonal, or irregular shaped. The opening of the annular fluid-absorption layer may or may not be centrally located in relation to the total surface area of the fluid-absorption layer. A transparent part of the wound dressing may, for example, be defined by or enclosed by the opening of an annular fluid-absorption layer. FIG. 6 depicts a wound dressing in which the fluid-absorption layer is an annular shape comprising an opening (X), that may be transparent to allow observation of the wound, completely surrounded by the fluid-absorption layer (Y).

The fluid-absorption layer may, for example, comprise two or more portions. Each portion, for example ail portions of the fluid-absorption layer, may be located in the peripheral area of the wound dressing. Each portion may be any suitable shape including, for example square, rectangular, circular oval, polygonal, or irregular shaped. Each portion may be the same or a different shape.

A transparent part of the wound dressing may, for example, be located between the two or more portions of the fluid-absorption layer. For example, a transparent part of the wound dressing may be located centrally to the two or more portions of the fluid-absorption layer. The two or more portions of the fluid-absorption layer may, for example, be distributed randomly across the surface area of the wound dressing. The two or more portions of the fluid-absorption layer may, for example, be positioned at regular intervals across the surface area of the wound dressing, for example around the periphery of the wound dressing.

Figure 7:
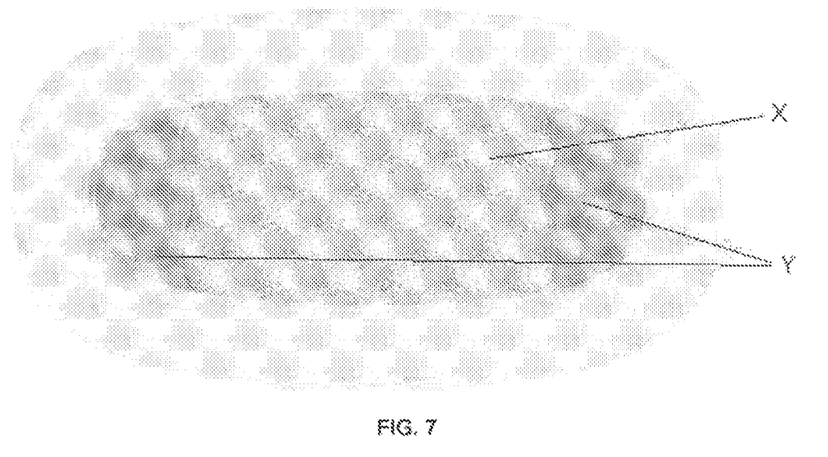

FIG. 7 depicts a wound dressing in which the fluid-absorption layer comprises two portions (Y) between which an opening (X) is located, which may be transparent to allow observation of the wound. The two fluid-absorption layers are located at the periphery of the wound dressing.

The fluid absorption layer may conform (touch) partially or completely with the perimeter of the wound dressing. The fluid-absorption layer may, for example, have a perimeter shape that is substantially the same as the perimeter shape of the wound dressing and be located inwards of the perimeter of the wound dressing.

The fluid-absorption layer advantageously has the capacity to absorb a high proportion of body fluids such as serum, blood or wound exudate.

The fluid-absorption layer may, for example, have a saline absorption capacity of at least about 50 wt % based on the total weight of the fluid-absorption layer. For example, the fluid-absorption layer may have a saline absorption capacity of at least about 75% or at least about 100% or at least about 125% or at least about 150% or at least about 175% or at least about 200% based on the total weight of the fluid-absorption layer.

The fluid-absorption layer may, for example, have a saline absorption capacity equal to or less than about 1000 wt % based on the total weight of the fluid-absorption layer. For example, the fluid-absorption layer may have a saline absorption capacity equal to or less than about 900 wt % or equal to or less than about 800 wt % or equal to or less than about 700 wt % or equal to or less than about 600 wt % or equal to or less than about 500 wt % or equal to or less than about 400 wt % based on the total weight of the fluid-absorption layer.

The fluid-absorption layer may, for example, comprise or consist of one or more of a foam, a hydrogel, a foamed hydrogel, a sponge, a polymer and a hydrocolloid.

A foam fluid-absorption layer is an open cell foam. The open cell foam may, for example, be a hydrophilic open cell foam. The open cell foam may, for example, have a cell size ranging from about 5 μm to about 700 μm, for example from about 10 μm to about 500 μm or from about 30 μm to about 400 μm or from about 50 μm to about 300 μm. The foam may, for example, have about 20% to about 70%, for example from about 30% to about 60% of the total surface area as openings. The open ceil foam permits transport of fluid secreted from the wound any cellular debris into and within the foam as well as between individual pieces of foam.

The foam may, for example, be selected from one or more of polyvinyl acetate, polyurethane, carboxylated butadiene-styrene rubber, polyacrylate, poly vinylic or cellulosic foams. Polyurethane foams may be prepared by reacting particular isocyanate-capped polyoxyethylene polyols having an isocyanate functionality greater than two with large amounts of an aqueous reactant, preferably water Polyvinylic foams include polyvinyl acetal foams formed by the reaction of polyvinyl alcohol and an aldehyde, usually formaldehyde or acetaldehyde. Such foams are generally hard until wetted by water, it is envisaged that such foams may be used dry or may be wetted and squeezed 'dry' whereupon they retain sufficient moisture to remain soft and flexible and are packaged in a waterproof package. Suitable foams may be prepared from hydrophilic materials per se or may be treated to render them hydrophilic, for example with surfactants. It is preferred however to use foams which are made of polymer which is itself hydrophilic. Such foams may be less likely to cause the wound exudate to coagulate rapidly. It is also within the scope of the—invention that a blend of two or more foams may be used or a combination of a foam with an absorption enhancing material such as, for example, a cellulose material in a form which is capable of being retained within the bag.

In certain embodiments, the fluid-absorption layer comprises or consists of polyurethane foam, for example hydrophilic polyurethane foam. The polyurethane foam may, for example, be an aromatic (formed from monomers comprising an aromatic group) or aliphatic (formed from monomers comprising an aliphatic group) polyurethane foam. The polyurethane foam may, for example, be a cross-linked hydrophilic polyurethane. The polyurethane foam may, for example, be made by reacting a hydrophilic isocyanate-terminated polyether prepolymer with water. The polyurethane foam may, for example, be a polyester or polyether polyurethane foam.

The foam may, for example, be a foamed hydrogel. The hydrogel may, for example, be as described herein.

The fluid-absorption layer may comprise or consist of a hydrogel. The hydrogel may, for example, be a hydrophilic monomer comprising at least one hydrophilic monomer and one or more other comonomers. The hydrogel may, for example, be cross-linked. The hydrogel may, for example, further comprise water and/or one or more additional additives selected from organic plasticisers, surfactants, polymers, pH regulators, electrolytes, chloride sources, bioactive compounds and mixtures thereof. The hydrogel may comprise 10 wt % or less of these additional additives. The hydrogel typically has a continuous structure in that it doesn't contain pores or have an internal cellular structure.

The hydrogel may be made from a precursor solution. Preferably, the precursor solution is aqueous. The precursor solution may comprise aqueous solutions of one or more monomers that are ionic, non-ionic, amphoteric, zwitterionic or combinations thereof.

The precursor solution preferably contains one or more monomers capable on polymerisation of forming a three-dimensional matrix of cross-linked polymer molecules. The expressions "polymer", "polymerisation" and like expressions, used herein, includes within its scope homopolymerisation and copolymerisation and the products thereof.

Optionally, the hydrogel is an ionic hydrogel, i.e. a hydrogel formed from ionic monomers. Optionally, the hydrogel, which may be an ionic hydrogel, comprises a hydrophilic polymer having multiple pendant sulphonyl groups, optionally with multiple pendant carboxylic groups. Optionally, at least some of the pendant sulphonyl groups are in salt form, for example associated with one or more cations, for example selected from sodium and potassium.

Examples of suitable monomers for use in forming the hydrogel, include: 2-acrylamido-2-methylpropane sulphonic acid or a substituted derivative thereof or a salt thereof (e.g. an ammonium or alkali metal salt such as sodium, potassium or lithium salts); acrylic acid or a substituted derivative thereof or a salt thereof (e.g. an alkali metal salt such as sodium, potassium or lithium salt); a polyalkylene glycol acrylate or a substituted derivative thereof; a polyalkylene glycol methacrylate or a substituted derivative thereof; acrylic acid (3-sulphopropyl) ester or a substituted derivative thereof or a salt thereof (e.g. an alkali metal salt such as sodium, potassium or lithium salt); diacetone acrylamide (N-1, 1-dimethyl-3-oxobutyl-acrylamide); a vinyl lactam (e.g. N-vinyl pyrrolidone or a substituted derivative thereof); an optionally substituted N-alkylated acrylamide such as hydroxyethyl acrylamide; and an optionally substituted N,N-dialkylated acrylamide; and/or N-acryloyl morpholine or a substituted derivative thereof. Preferably, the polymerisable monomer is selected from the 2-acryiamido-2-methylpropane sulphonic acid, which is optionally in salt form, for example associated with one or more cations, for example selected from sodium and potassium; acrylic add (3-sulphopropyl) ester, which is optionally in salt form, tor example associated with one or more cations, for example selected from sodium and potassium; N-acryloyl morpholine; and hydroxyethyl acrylamide.

The hydrogel may comprise a plasticised three-dimensional matrix of cross-linked polymer molecules, and has sufficient structural integrity to be self-supporting even at very high levels of internal water content, with sufficient flexibility to conform to the surface contours of mammalian skin or other surface with which it is in contact.

The hydrogel generally comprises, in addition to the cross-linked polymeric network an aqueous or nan-aqueous plasticising medium including an organic plasticiser. This plasticising medium is preferably present in the same precursor solution as the monomer(s), although if desired it may be applied to the fibrous material separately from the monomer(s) but before polymerisation. In the material to be polymerised, the precursor solution preferably composes the monomer(s), cross-linking agent, plasticiser, which may be an organic plasticiser, and optionally water and other ingredients as desired. The polymerisation reaction is preferably a free-radical polymerisation with cross-linking, which may for example be induced by light, heat, radiation (e.g. ionising radiation), or redox catalysts, as is well known.

For example, the free radical polymerisation may be initiated in known manner by light (photoinitiation), particularly ultraviolet light (UV photoinitiation); heat (thermal initiation); electron beam (e-beam initiation); ionising radiation, particularly gamma radiation (gamma initiation); non-ionising radiation, particularly microwave radiation (microwave initiation); or any combination thereof. The precursor solution may include appropriate substances (initiators), at appropriate levels, e.g. up to about 5% by weight, more particularly between about 0.002% and about 2% by weight, which serve to assist the polymerisation and its initiation, in generally known manner. Preferred photoinitiators include any of the following either alone or in combination.

Type I-a-hydroxy-ketones and benzilidimethyi-ketals e.g. Irgacure 651. These are believed on irradiation to form benzoyl radicals that initiate polymerisation Photoinitiators of this type that are preferred are those that do not carry substituents in the para position of the aromatic ring Examples include Irgacure 184 and Daracur 1173 as marketed by Ciba Chemicals, as well as combinations thereof.

A particularly preferred photoinitiator is 1-hydroxy cyclohexyl phenyl ketone: for example, as marketed under the trade name Irgacure 184 by Ciba Speciality Chemicals. Also preferred are (available under the trade name Daracur 1173) and mixtures of 1-hydroxycyclohexyl phenyl ketone and 2-hydroxy-2-propyl phenyl keton, for example mixtures of Irgacure 184 and Daracur 1173.

Photo-polymerisation is particularly suitable, and may be achieved using light, optionally together with other Initiators, such as heat and/or ionizing radiation Photoinitiation will usually be applied by subjecting the pre-reaction mixture containing an appropriate photoinitiation agent to ultraviolet (UV) light. The incident UV Intensity, at a wavelength in the range from 240 to 420 nm, is typically greater than about 10 mW/cm$^2$. The processing will generally be carried out in a controlled manner involving a precise predetermined sequence of mixing and thermal treatment or history. The UV irradiation time scale should ideally be less than 60 seconds, and preferably less than 10 seconds to form a gel with better than 95% conversion of the monomers. Those skilled in the art will appreciate that the extent of irradiation will be dependent on a number of factors, including the UV intensity, the type of UV source used, the photoinitiator quantum yield, the amount of monomer(s) present, the nature of the monomer(s) present and the presence of polymerisation inhibitor.

After completion of the polymerisation and optionally after conversion into a wound dressing, the hydrogel is preferably sterilised in conventional manner.

If desired, certain ingredients of the hydrogel may be added after the polymerisation and optional cross-linking reaction. However, it is generally preferred that substantially all of the final ingredients of the hydrogel are present in the precursor solution, and that—apart from minor conventional conditioning or, in some cases, subsequent modifications caused by the sterilisation procedure—substantially no chemical modification of the hydrogel takes place after completion of the polymerisation reaction.

Monomers

Optional substituents of the monomers used to prepare the hydrogels used in the present invention may preferably be selected from substituents which are known in the art or are reasonably expected to provide polymerisable monomers which form hydrogel polymers having the properties necessary for the present invention. Suitable substituents include, for example, lower (e.g. Ci to C5) alkyl, hydroxy, halo and amino groups.

Particularly preferred monomers include: the sodium salt of 2-acrylamido~2~methylpropane sulphonic acid, commonly known as NaAMPS, which is available commercially at present from Lubrizol as either a 50% aqueous solution (reference code LZ2405) or a 58% aqueous solution (reference code L22405A); acrylic acid (3-sulphopropyl) ester potassium salt, commonly known as SPA or SPAK (SPA or SPAK is available commercially in the form of a pure solid from Raschig); N-acryloyl morpholine; and hydroxyethyl acrylamide.

Cross-linking Agents

Conventional cross-linking agents can be used to provide the necessary mechanical stability and to control the adhesive properties of the hydrogel. The amount of cross-linking agent required will be readily apparent to those skilled in the art such as from about 0.01% to about 0.5%, particularly from about 0.05% to about 0.4%, most particularly from about 0.08% to about 0.3%, by weight of the total polymerisation reaction mixture. Typical cross-linkers include tripropylene glycol diacrylate, ethylene glycol dimethacrylate, triacrylate, polyethylene glycol diacrylate (polyethylene glycol (PEG) molecular weight between about 100 and about 4000, for example PEG400 or PEG600), and methylene bis acrylamide.

Organic Plasticisers

One or more organic plasticisers may be present in the hydrogel and/or the hydrogel precursor solution. The one or more organic plasticisers, when present, may suitably comprise any of the following either alone or in combination: at least one polyhydric alcohol (such as glycerol, polyethylene glycol, or sorbitol), at least one ester derived therefrom, at least one polymeric alcohol (such as polyethylene oxide) and/or at least one mono- or poly-alkylated derivative of a polyhydric or polymeric alcohol (such as alkylated polyethylene glycol). Glycerol is the preferred plasticiser. An alternative preferred plastticiser is the ester derived from boric acid and glycerol. When present, the organic plasticiser may comprise up to about 45% by weight of the hydrogel composition.

Surfactants

Any compatible surfactant may optionally be used as an additional ingredient of the hydrogel composition. Surfactants can lower the surface tension of the mixture before polymerisation and thus aid processing. The surfactant or surfactants may be non-ionic, anionic, zwitterionic or cationic, alone or In any mixture or combination. The surfactant may itself be reactive i.e. capable of participating in the hydrogel-forming reaction. The total amount of surfactant, if present, is suitably up to about 10% by weight of the hydrogel composition, preferably from about 0.05% to about 4% by weight. In a preferred embodiment, of the invention the surfactant comprises at least one propylene oxide/ethylene oxide block copolymer, for example such as that supplied by BASF Plc under the trade name Pluronic P65 or L64.

Other Additives

The hydrogel may include one or more additional ingredients, which may be added to the pre-polymerisation mixture or the polymerised product, at the choice of the skilled worker Such additional ingredients may be selected from additives, including, for example, water, organic plasticisers, surfactants, polymeric material (hydrophobic or hydrophilic in nature, including proteins, enzymes, naturally occurring polymers and gums), synthetic polymers with and without pendant carboxylic acids, electrolytes, pH regulators, colorants, chloride sources, bioactive compounds and mixtures thereof. The polymers can be natural polymers (e.g. xanthan gum), synthetic polymers (e.g. polyoxypropylene-polyoxyethylene block copolymer or poly-(methyl vinyl ether maleic anhydride)), or any combination thereof. "Bioactive compounds" may indicate any compound or mixture included within the hydrogel for some effect it has on living systems, whether the living system be bacteria or other microorganisms or higher animals such as the patient.

Bioactive compounds that may be mentioned include, for example, pharmaceutically active compounds, antimicrobial agents, antiseptic agents, antibiotics and any combination thereof.

Antimicrobial agents may, for example include: sources of oxygen and/or iodine (e.g. hydrogen peroxide or a source thereof and/or an iodide salt such as potassium iodide) (see, for example Bioxzyme™ technology, for example in The Sunday Telegraph (UK) 26 Jan. 2003 or the discussion of the Oxyzyme™ system at www.wounds-uk.com/posterabstracfs2003.pdf); honey (e.g. active Manuka honey); antimicrobial metals, metal ions and salts, such as, for example, silver-containing antimicrobial agents (e.g. colloidal silver, silver oxide, silver nitrate, silver thiosulphate, silver sulphadiazine or any combination thereof); or any combination thereof. Hydrogels incorporating antimicrobial agents may, for example, be active against such organisms as *Staphylococcus aureus* and *Pseudomonas aeruginosa*.

Agents for stimulating the healing of wounds and/or for restricting or preventing scarring may be incorporated into the hydrogel. Examples of such agents include growth factors e.g. from GroPep Ltd, Australia or Procyte, USA (see, e.g. WO-A-98/02270, the contents of which are incorporated herein by reference); cell nutrients (see, e.g., WO-A-93/04691, the contents of which are incorporated herein by reference); glucose (see, e.g., WO-A-93/10795, the contents of which are incorporated herein by reference); an anabolic hormone or hormone mixture such as insulin, triiodothyronine, thyroxine or any combination thereof (see, e.g., WO-A-93/04691, the contents of which are incorporated herein by reference); or any combination thereof.

Additional polymer(s), typically rheology modifying polymer(s), may be incorporated into the polymerisation reaction mixture at levels typically up to about 10% by weight of total polymerisation reaction mixture, e.g. from about 0.2% to about 10% by weight. Such polymer(s) may include polyacrylamide, poly-NaAMPS, polyethylene glycol (PEG), polyvinylpyrrolidone (PVP) or carboxymethyl cellulose.

The hydrogel may consist essentially of a cross-linked hydrophilic polymer of a hydrophilic monomer and optionally one or more comonomer, together with water and/or one or more organic plasticiser, and optionally together with one or more additives selected from surfactants, polymers, pH regulators, electrolytes, chloride sources, bioactive compounds and mixtures thereof, with less than about 10% by weight of other additives.

The hydrogel may be formed by disposing a layer of precursor solution on a substrate, then curing the precursor solution to form the hydrogel, and cutting portions of the hydrogel. For further details of the hydrogel material for use in the present invention, and its preparation, please refer to the following publications: PCT Patent Applications Nos WO-37/24149, WO-97/34947, WO-00/06214, WO-00/06215, WO-00/07638, WO-00/48319, WO-00/65143 and WO-01/96422, the disclosures of which are incorporated herein by reference.

The fluid-absorption layer may, for example, comprise or consist of sponge material. The sponge material may, for example, be made from cellulose wood fibres or foamed plastic polymers. The sponge material may, for example, be a natural sponge.

The fluid-absorption layer may, for example, comprise or consist of a superabsorbent polymer (SAP). The superabsorbent polymer may for example, comprise acrylonitrile polymer grafted onto the backbone of starch molecules. The superabsorbent polymer may, for example, comprise polyacrylic acid (e.g. sodium polyacrylate). The superabsorbent polymer may, for example, comprise polyacrylamide copolymer, ethylene maleic anhydride copolymer, cross-linked carboxy methyl cellulose, polyvinyl alcohol copolymers, cross-linked polyethylene oxide and starch grafted copolymer of polyacrylonitrile.

The superabsorbent polymer may, for example, be made by gel polymerization, suspension polymerization or solution polymerization.

The fluid-absorption layer may, for example, comprise or consist of a hydrocolloid. The hydrocolloid may, for example, be a rubber based hydrocolloid. The hydrocolloid may, for example, compose a cross-linked adhesive mass of a dispersion of gelatin, pectin and carboxy-methylcellulose together with other polymers and adhesives. Upon contact with water, the polysaccharides and other polymers absorb water and swell, forming a gel.

Optionally, the absorbent layer comprises or consists of fibres Optionally, the fibres form a gel when hydrated, which are sometimes termed gel-forming fibres in the art.

Optionally, the fibres comprise an alginate, chitosan or a cellulose derivative or any combination thereof. Preferred types of fibre compose calcium alginate (available from, for example, Foshan United Medical Technologies Ltd, China), and/or sodium polymethacrylate (available for example, under the tradename Oasis™ from Technical Absorbents Limited). Optionally, the fibres comprise an alginate, optionally calcium alginate, containing in its polysaccharide chain guluronic and/or mannuronic acid, and optionally with a molar ratio of guluronic to mannuronic acid from 90:10 to 10:90, more preferably from 30:20 to 20:80 and even more preferably from 80:20 to 30:70. A particularly preferred fibre comprises an alginate comprising one or more of the following ions, calcium, sodium, zinc and silver. The cellulose derivative may comprise, for example, hydroxypropylmethyl cellulose or carboxymethyl cellulose.

The fluid-absorption layer may, for example, have a thickness of at least about 10 µm. For example, the fluid-absorption layer may have a thickness of at least about 20 µm or at least about 50 µm or at least about 100 µm. The fluid-absorption layer may, for example, have a thickness equal to or less than about 800 µm. For example, the fluid-absorption layer may have a thickness equal to or less than about 700 µm or equal to or less than about 600 µm or equal to or less than about 500 µm or equal to or less than about 400 µm or equal to or less than about 300 µm.

Fluid-Wicking Layer

The fluid-wicking layer acts to move fluid from the wound by capillary action towards the fluid-absorption layer of the wound dressing. The fluid-wicking layer is preferably located on the wound-facing side of the fluid-absorption layer and wound dressing.

The whole of or a part of the fluid-wicking layer may be transparent, as defined herein.

The fluid-wicking layer is preferably positioned such that it overlays the wound and/or peri-wound area of the wound when the wound dressing is in use. This is so the fluid from the wound is directly absorbed by the fluid-wicking layer without contacting any other area of the surrounding skin. The fluid-wicking layer may therefore be located partially or fully in a central area of the wound dressing (e.g. in the central 50% of the surface area of the wound dressing). Where the fluid-absorption layer is located at the laterally to the fluid-wicking layer it may be located at the periphery of the wound dressing.

The fluid-wicking layer may, for example, partially or completely overlay the fluid-absorption layer. The fluid-wicking layer may, for example, partially or completely overlay the breathable film.

The fluid-wicking layer may be of any suitable size and shape. The fluid-wicking layer may, for example, be continuous in that it is formed from a single portion of material. Alternatively, the fluid-wicking layer may comprise two or more portions.

The fluid-wicking layer may, for example, cover at least about 50% of the surface area of the wound dressing. For example, the fluid-wicking layer may cover at least about 55% or at least about 80% or at least about 85% or at least about 70% or at least about 75% of the surface area of the wound dressing. For example, the fluid-wicking layer may cover up to about 100% or up to about 99% or up to about 98% or up to about 95% or up to about 90% of the surface area of the wound dressing.

The fluid-wicking layer may have a fluid-absorption capacity that is less than the fluid-absorption capacity of the fluid-absorption layer. For example, the fluid-wicking layer may have a saline absorption capacity equal to or less than about 100 wt % based on the total weight of the fluid-wicking layer. For example, the fluid-wicking layer may have a saline absorption capacity equal to or less than about 95 wt % or equal to or less than about 90 wt % or equal to or less than about 85 wt % or equal to or less than about 80 wt % or equal to or less than about 75 wt % based on the total weight of the fluid-wicking layer. For example, the fluid-wicking layer may have a saline absorption capacity equal to or greater than about 10 wt % or equal to or greater than about 15 wt % or equal to or greater than about 20 wt % or equal to or greater than about 25 wt % based on the total weight of the fluid-wicking layer.

The fluid-wicking layer may, for example, be a woven fabric, a non-woven fabric or a polymer having channels formed therein. The woven fabric, non-woven fabric or polymer having channels formed therein may, for example, be hydrophilic in nature.

The fluid-wicking layer may, for example, be a mesh (a barrier made of connected fibres). The mesh may, for example, be naturally hydrophilic or may be coated with a hydrophilic coating. The hydrophilic coating may, for example, be a hydrophilic polymer coating. The fluid-wicking layer may, for example, be a surgical mesh.

The fluid-wicking layer (e.g. woven or non-woven fabric) may, for example, be formed of any suitable natural or synthetic material, including, for example, polymers (e.g. polymer fibres) such as polypropylene, polymers made from polyglycolic acid and prolene, polyvinylidene fluoride, polytetrafluoroethylene and polyethylene terephthalate. The fluid-wicking layer (e.g. woven or non-woven fabric) may, for example, be made of fibres comprising one or more of cellulose, lignin, cotton, hemp, jute, flax, wood fibre, Silk (e.g. from silkworm or spider), wool, fibrous proteins such as collagen.

The fluid-wicking layer may, for example, be formed from a hydrophilic material having channels formed therein. The channels have a size suitable to move fluid from the wound through the fluid-wicking layer to the fluid-absorption layer. The hydrophilic material may, for example, be a polymer. The hydrophilic material suitable to have channels formed therein may, for example, be a hydrogel. The hydrogel may, for example, be as defined herein in relation to the fluid-absorption layer. The hydrophilic material suitable to have channels formed therein may, for example, be an adhesive.

The fluid-wicking layer may, for example, have a thickness of at least about 10 μm. For example, the fluid-wicking layer may have a thickness of at least about 20 μm or at least about 50 μm or at least about 100 μm. The fluid-wicking layer may, for example, have a thickness equal to or less than about 800 μm. For example, the fluid-wicking layer may have a thickness equal to or less than about 700 μm or equal to or less than about 600 μm or equal to or less than about 500 μm or equal to or less than about 400 μm or equal to or less than about 300 μm.

Adhesive Layers

The wound dressing may, for example, comprise one or more layers of adhesive. The adhesive may be used to hold or assist in holding the layers of the wound dressing together. However, some layers of the wound dressing may be Inherently adhesive. Additional adhesive layers therefore may not be required to hold some layers of the wound dressing together.

An adhesive layer may, for example, be present between the breathable film and the fluid-absorption layer. Alternatively or additionally, an adhesive layer may be present between the fluid-absorption layer and the fluid-wicking layer.

An adhesive layer may, for example, be present on the outermost wound-facing side of the wound dressing to adhere the wound dressing to the skin of the patient. The skin adhesive is preferably applied to the periphery of the wound dressing such that in use, the adhesive does not contact the wound or pen-wound area. The skin adhesive may, for example, be discontinuous or continuous. The skin adhesive may, for example, have an area of 5% to 95% of the total surface area of the wound dressing.

The adhesive may, for example, be breathable in that it allows the passage of gases therethrough but not the passage of liquids. The adhesive may, for example, be a medical grade adhesive. The adhesive may, for example, be a pressure sensitive adhesive. The adhesive may, for example, be a medical grade pressure sensitive adhesive. The adhesive may, for example, comprise one or more of acrylic, rubber, silicone, polyurethane or hybride.

The adhesive may be used in a sufficient amount to adhere two layers of the wound dressing together. The adhesive may, for example, be disposed across an entire surface of at least one of the layers to be adhered together. Alternatively, the adhesive may be disposed across only part of one or both of the layers to be adhered together.

The coat weight of the adhesive layer may, for example, range from about 5 g/m$^2$ to about 300 g/m$^2$. For example, the coat weight of the adhesive layer may range from about 10 g/m$^2$ to about 200 g/m$^2$ or from about 20 g/m$^2$ to about 100 g/m$^2$ or from about 20 g/m$^2$ to about 80 g/m$^2$.

Non-Absorbent Waterproof Layer

A non-absorbent waterproof layer may, for example, be used to prevent fluid from the fluid-absorption layer from being in contact with the skin. The non-absorbent waterproof layer may therefore be present on the wound-facing side of the fluid-absorption layer. The non-absorbent waterproof layer may also be on the wound-facing side of the fluid-wicking layer. The non-absorbent waterproof layer may not cover a transparent part of the wound dressing.

The non-absorbent waterproof layer does not allow fluid to be transmitted through it. The non-absorbent waterproof layer therefore may also be a skin adhesive layer. The non-absorbent waterproof layer may, for example, be an adhesive, a hydrogel or a polymer film, for example as described above. The non-absorbent waterproof layer may, for example, be a silicone gel, a hydrogel, a polyurethane adhesive, an acrylic adhesive, a hydrocolloid, a rubber adhesive, a polyethylene film, a polyurethane film or an ethyl methyl acrylate film.

Since it Is necessary to allow fluid to be transported from the wound to the wound dressing, the non-absorbent waterproof layer does not cover the entire wound-facing surface of the wound dressing. The non-absorbent waterproof layer may have a surface area that is equal to or less than about 75% of the total surface area of the wound dressing. For example, the non-absorbent waterproof layer may have a surface area that is equal to or less than about 70% or equal to or less than about 65% or equal to or less than about 60% or equal to or less than about 55% or equal to or less than about 50% or equal to or less than about 45% or equal to or less than about 40% of the total surface area of the wound dressing. For example, the non-absorbent waterproof layer may have a surface area that is at least about 5% or at least about 10% or at least about 15% or at least about 20% or at least about 25% of the total surface area of the wound dressing. The non-absorbent waterproof layer may, for example, completely overlay the fluid-absorption layer.

The non-absorbent waterproof layer may, for example, have a thickness ranging from about 1 μm to about 100 μm, for example from about 5 μm to about 90 μm or from about 10 μm to about 50 μm.

Liners

The wound dressing may, for example, further comprise one or more liner (release liner). The liner is positioned on the outermost wound-facing side of the wound dressing and is removed from the dressing before use. The liner acts to facilitate ease of handling and packaging. The liner may, for example, assist in maintaining the wound dressing in a sterile condition. The liner may, for example, cover the entire surface of the wound dressing. The liner may, for example, cover only the surface of the wound dressing where an adhesive portion is exposed. The liner may, for example, compose a silicone on the surface.

Uses

The wound dressings described herein may be used for treating or preventing a wound. Thus, there is provided herein methods of treating or preventing a wound and wound dressings for use in treating or preventing a wound. Treating or preventing a wound comprises applying the wound dressing to the wound.

The phrase "treating or preventing" refers to all forms of healthcare intended to remove or avoid the wound or to relieve its symptoms, including preventive and curative care, as judged according to any of the tests available according to the prevailing medical practice. An intervention that aims with reasonable expectation to achieve a particular result but does not always do so is included within the expression "treating or preventing". An intervention that succeeds in accelerating progression of wound healing is included within the expression "treating or preventing". The phrase "treating or preventing" in relation to a wound includes the initiation and/or maintenance and/or acceleration of all stages of wound healing (including hemostasis, inflammation, proliferation, maturation). However, the wound dressings described herein may be particularly used during stages of wound healing involving exudation of fluid from the wound.

The wound dressings described herein may be useful in treating or preventing various types of wound, primarily open wounds. The term wound includes skin cuts, grazes abrasions, tears, burns, scalds, ulcers, spots, blisters and chafes, whether dermal, epidermal, or a combination of both. The wound may or may not be infected or contaminated. The wound may, for example, be chronic or acute. The wound may, for example, be a high exudating wound.

The wound dressings described herein may also be used for securing a device that has been inserted through the skin of a subject. Thus, there is provided herein methods of securing a device that is at least partially (e.g. fully) inserted in the skin of a subject and wound dressings for use in securing a device that is at least partially (e.g. fully) inserted in the skin of a subject. Securing the device comprises applying the wound dressing to the area where the device has been inserted in the skin. The device may, for example, be a catheter.

Methods of Manufacture

There is also provided herein methods of manufacturing the wound dressings described herein. The methods comprise adhering the layers of the wound dressing to each other to form a multilayer structure.

Each of the individual layers of the wound dressing may be made by methods known to those skilled in the art. The individual layers may be sourced separately and then adhered together in the desired form. Alternatively, one or more of the layers of the wound dressing may be made concurrently, for example in situ. Each of the layers may be adhered to the adjacent layer separately or all the layers in the wound dressing may be adhered to each other at once. The layers may, for example, be adhered to each other by application of heat and/or pressure.

The foregoing broadly describes certain embodiments of the present invention without limitation. Variations and modifications as will be readily apparent to those skilled in the art are intended to be within the scope of the present invention as defined in and by the appended claims.

EXAMPLES

Exemplary wound dressings having the structures shown in FIGS. 1 to 5 were made using the materials specified in the Tables below. Dressings 1, 3 and 5 are according to the invention Dressings 2 and 4 are comparative dressings.

The dressings were tested for fluid absorption using two different test models described below.

Dynamic Wound Model

An inox plate perfectly horizontal is perforated with a 8 mm diameter hole. In the hole a tubing connected to a pump is used to deliver saline solution. The saline solution consist of a solution of sodium/calcium chloride containing 142 mmol/l of sodium ions and 2.5 mmol/l of calcium ions, values typical of those found in serum. On top of the 8 mm diameter hole 2 absorbent pads (Merk Millipore, ref. AP1004700) are placed and pre-wetted with saline solution. Those pads assure that the saline solution will spread and are representative of a wound. The experiment is conducted in a temperature humidity controlled environment (23° C./50% relative humidity). The dressing is placed on the dynamic wound model in such a way as to have the wound simulating absorbent pads positioned in the centre of the dressing. The dressing is weighted before application to the dynamic wound model ($W_{dry}$). A constant flow of saline/calcium solution is delivered to the wound dressing for a duration of 24 hours. At the end of the test, the pump is stopped; the total volume of saline solution dispensed during the experiment is recorded ($W_{saline}$). The dressing is carefully removed from the dynamic wound model and weighted ($W_{wet}$). Any fluid left over on the dynamic wound model is wicked using towel and weighted ($W_{left\ over}$). The dressing is then placed on absorbent towels, a 5 Kg weight is place on top of it for 1 minute. At the end the dressing is weighted again ($W_{ret}$).

The following can then be calculated:

Total fluid absorbed by the dressing (%): $[(W_{wet}-W_{dry})/W_{saline}]\times 100$ The fluid absorbed free, which is the fluid absorbed but not retain within the dressing under pressure (%): $[(W_{wet}-W_{ret})/W_{saline}]\times 100$ The fluid absorbed locked, the fluid absorbed and retained within the dressing under pressure (%); $[(W_{ret}-W_{dry})/W_{saline}]\times 100$ The fluid not managed by the dressing: $[W_{left\ over}/W_{saline}]\times 100$ The fluid evaporated: $[(W_{saline}-W_{wet}-W_{left\ over})/W_{saline}]\times 100$ Vertical Leg Model A rigid cylinder 34.5 cm in circumference was used as a leg model. A 5.5 mm hole was drilled centrally in the cylinder which allowed a 6 mm PVC tube to form an interference fit with the cylinder wall. A filter paper (Whatman 41. Whatman International Ltd. Maid-stone, UK) 50 mm in diameter was placed centrally over the tube where it exited flush with the cylinder surface to facilitate initial spreading of the test fluid, and simulate a wound of a reasonable size.

Test fluid was delivered at a constant rate by means of a syringe driver (Cole Parmer 78-9100C. Cole Parmer, Vernon Hills, IL) fitted with a Plastipak 60 ml syringe (BD, Drogheda, Ireland). A flow rate of 1 ml/hour and 1.5 ml/h were selected to represent, a highly exuding wound. The saline solution consists of a solution of sodium/calcium chloride containing 142 mmol/l of sodium ions and 2.5 mmol/l of calcium ions, values typical of those found in serum.

The leg model was placed in an incubator at 34° C. (skin temperature) with either an appropriate salt solution to maintain a relative humidity of 56%-62%, or a tray of silica gel to reduce the relative humidity to around 33%-38%. Both temperature and humidity within the chamber were monitored using an Easy Log EL-USB-2 data logger (Lascar Electronics, Salisbury, UK).

The dressing to be tested is weighed before application to the test rig ($W_{dry}$) and immediately following the completion of the test ($W_{wet}$). The total fluid dispensed into the dressing in the course of the test is calculated ($W_{total}=24\times$ Flow rate). The dressing is then placed on absorbent towels, a 5 Kg weight is place on top of it for 1 minute. At the end the dressing is weighted again ($W_{ret}$).

The following can then be calculated:

Total weight of liquid applied to the dressing: $24\times$Flow rate

Weight of fluid absorbed in the dressing: $W_{wet}-W_{dry}$

Weight of fluid locked in the dressing: $W_{ret}-W_{dry}$

Weight of fluid lost by evaporation: $W_{total}-(W_{wet}-W_{dry})$

Table 1 shows the result of the dynamic wound model for wound dressings having the composition shown in Table t and the structure depicted in one of FIGS. 1 to 5.

Figure 1:
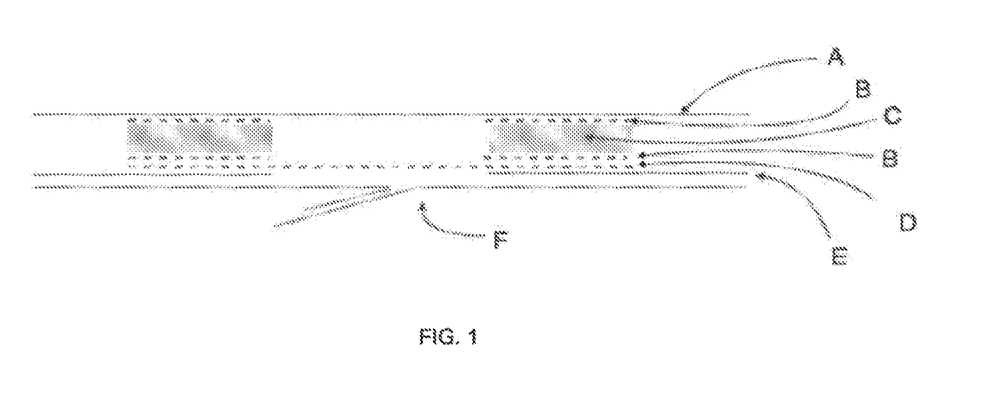
FIGS. 1, 3 and 5 to 7 depict, without limitation, particular embodiments of the wound dressings of the present invention.
Figure 2:
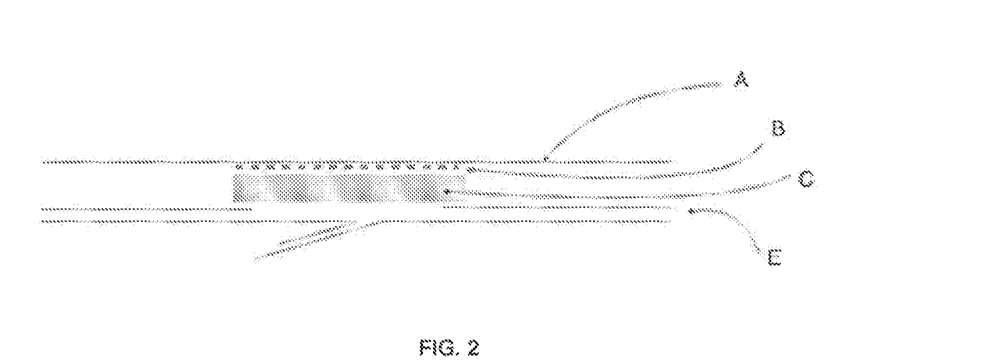
FIGS. 2 and 4 depict comparative wound dressings.
Figure 3:
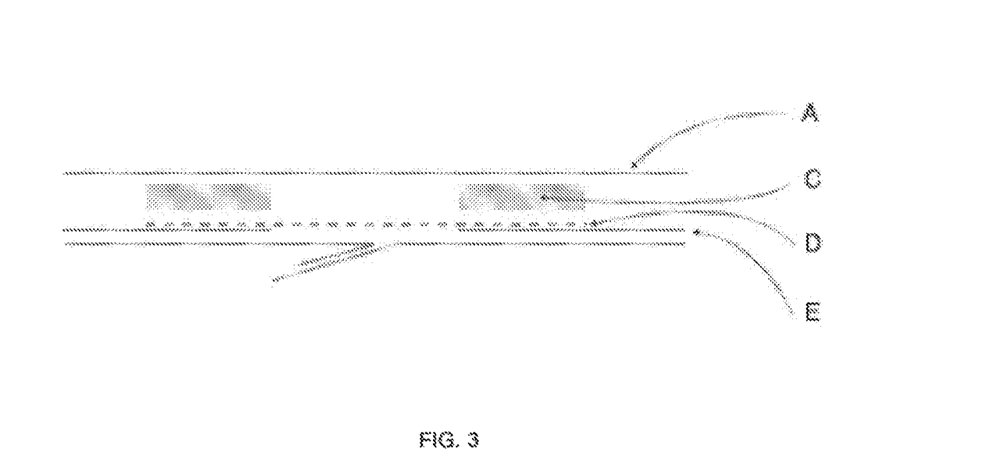
Figure 4:
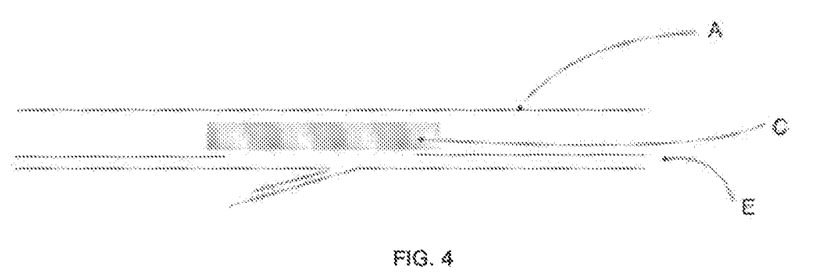
Figure 5:
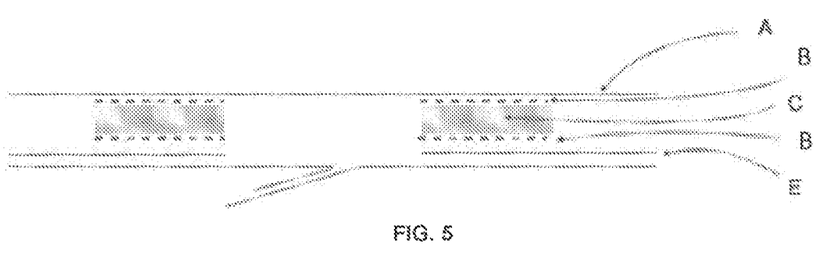

Table 2 shows the result of the vertical leg model for wound dressings having the composition shown in Table 1 and the structure depicted in one of FIGS. 1 and 2.

TABLE 1

| Dressing construction (FIG.) | | 2 | 1 | 2 | 1 | 5 | 4 | 3 |
|---|---|---|---|---|---|---|---|---|
| layer | Material | | | | | | | |
| A | Polyurethane film (Inspire film 2327) | X | X | X | X | X | X | X |
| B | Transfer tape of acrylic adhesive (Scapa RX1240U) | X | X | X | X | X | X | X |
| C | Rubber based hydrocolloid essentially based on SIS rubber mixed with carboxymethyl cellulose (Scapa Healthcare) | | | | | | X | X |
| | Hydrophilic polyurethane foam 2 mm thick (Corpura code: 5000093) | X | X | X | X | X | | |
| | Sponge of foamed AMPS-based hydrogel (Scapa Healthcare gel301) | | | | | | | |
| D | Double layer of open mesh fabric (polyester and polyamide) coated with a hydrophilic treatment (SEFAR Meditex) | | X | | X | | | X |
| E | Silicon gel coated on a polyurethane film backing with an acrylic adhesive on the other face (Scapa Rx1401S) | X | X | X | X | X | X | X |
| Dynamic Wound Model | | | | | | | | |
| Total Fluid injected in dressing (g) | | 57* | 57* | 36** | 36** | 36** | 12 | 12 |
| Total fluid non absorbed by the dressing (g) | | 0 | 0 | 0 | 0 | 11.1 | 0 | 0 |
| Total fluid in dressing (g) | | 14.5 | 7.2 | 25.0 | 21.1 | 11.8 | 8.10 | 5.09 |
| Free fluid in dressing (g) | | 8.3 | 4.2 | 17.6 | 15.4 | 7.0 | 1.64 | 1.24 |
| Locked fluid in dressing (g) | | 6.2 | 3.0 | 7.4 | 5.7 | 4.8 | 6.46 | 3.85 |
| Fluid evaporated (g) | | 42.5 | 49.8 | 11.0 | 14.9 | 13.1 | 3.90 | 6.91 |

(*) = Flow rate 1 ml/h
(**) Flow rate 1.5 ml/h
(***) Dressing could not handle fluid and leaked

TABLE 2

| Dressing construction (FIG.) | | 2 | 1 | 2 | 1 | 2 | 1 |
|---|---|---|---|---|---|---|---|
| Layer | Material | | | | | | |
| A | Polyurethane film (Inspire film 2327) | X | X | X | X | X | X |
| B | Transfer tape of acrylic adhesive (Scapa RX1240U) | X | X | X | X | X | X |

TABLE 2-continued

| Dressing construction (FIG.) | 2 | 1 | 2 | 1 | 2 | 1 |
|---|---|---|---|---|---|---|
| C Rubber based hydrocolloid essentially based on SIS rubber mixed with carboxymethyl cellulose (Scapa Healthcare) | | | | | | |
| Hydrophilic polyurethane foam 2 mm thick (Corpura code: 5000093) | X | X | | | X | X |
| Sponge of foamed AMPS-based hydrogel (Scapa Healthcare gel301) | | | X | X | | |
| D Double layer of open mesh fabric (polyester and polyamide) coated with a hydrophilic treatment (SEFAR Meditex) | | X | | X | | X |
| E Silicone gel coated on a polyurethane film backing with an acrylic adhesive on the other face (Scapa Rx1401S) | X | X | X | X | X | X |
| Vertical Leg Model | | | | | | |
| Total Fluid injected in dressing (g) | 23* | 23* | 34** | 34** | 34** | 34** |
| Total fluid in dressing (g) | 5.39 | 1.78 | 14.05 | 7.35 | Failed*** | 6.43 |
| Free fluid in dressing (g) | 2.46 | 0.48 | 1.29 | 0.18 | Failed*** | 2.57 |
| Locked fluid in dressing (g) | 2.93 | 1.30 | 12.76 | 7.17 | Failed*** | 3.86 |
| Fluid evaporated (g) | 17.61 | 21.22 | 19.95 | 26.65 | Failed*** | 27.57 |

(*) = Flow rate 1 ml/h
(**) Flow rate 1.5 ml/h
(***) Dressing could not handle fluid and leaked

The invention claimed is:

1. A wound dressing comprising a transparent part that enables observation of a wound, wherein the wound dressing comprises:
   a transparent breathable film;
   a fluid-absorption layer; and
   a transparent fluid-wicking layer for directing fluid towards the fluid-absorption layer;
   wherein the fluid-wicking layer is continuous and completely overlays the breathable film;
   wherein the fluid-absorption layer has a saline absorption capacity of at least 50 wt % based on the weight of the fluid-absorption layer;
   wherein the fluid-absorption layer is positioned between the breathable film and the fluid-wicking layer;
   wherein the fluid-absorption layer encloses the transparent part of the wound dressing that enables observation of the wound; and
   wherein the fluid-absorption layer is positioned laterally to the fluid-wicking layer and breathable film.

2. The wound dressing of claim 1, wherein the breathable film has a moisture vapour transmission rate equal to or greater than about 400 g/m2/24 h, wherein the breathable film has a thickness ranging from about 5 μm to about 300 μm, or wherein the breathable film has a moisture vapour transmission rate equal to or greater than about 400 g/m2/24 h and a thickness ranging from about 5 μm to about 300 μm.

3. The wound dressing of claim 1, wherein the fluid-absorption layer has a saline absorption capacity of at least 100 wt %.

4. The wound dressing of claim 1, wherein the fluid-absorption layer is a hydrocolloid, a foam, a hydrogel, a foamed hydrogel, a sponge, a superabsorbent polymer, or a combination thereof.

5. The wound dressing of claim 1, wherein the fluid-absorption layer is a polyurethane foam or a polyvinyl acetate foam.

6. The wound dressing of claim 1, wherein the fluid-absorption layer is positioned at a peripheral area of the wound dressing.

7. The wound dressing of claim 1, wherein the fluid-absorption layer has a thickness ranging from about 0.1 mm to about 0.5 mm.

8. The wound dressing of claim 1, wherein the fluid-absorption layer has a surface area of at least 5% of the total surface area of the wound dressing.

9. The wound dressing of claim 1, wherein the transparent fluid-wicking layer of the wound dressing is positioned at a central area of the wound dressing.

10. The wound dressing of claim 1, wherein the wound dressing includes a single fluid-absorption layer, and the fluid-absorption layer is a continuous layer.

11. The wound dressing of claim 1, wherein the fluid-absorption layer is annular and the transparent part of the wound dressing that enables observation of the wound is in a central position to the fluid-absorption layer.

12. The wound dressing of claim 1, wherein the fluid-absorption layer comprises two portions, wherein the transparent part of the wound dressing that enables observation of the wound is positioned between the two portions of the fluid-absorption layer.

13. The wound dressing of claim 1, wherein the fluid-wicking layer is located in the central 50% of the surface area of the wound dressing.

14. The wound dressing of claim 1, wherein the fluid-wicking layer covers at least 75% of the surface area of the wound dressing.

15. A method of treating a wound, the method comprising applying the wound dressing of claim 1 to the wound.

16. A method of securing a device that has been at least partially inserted through skin, the method comprising applying the wound dressing of claim 1 to the skin where the device has been at least partially inserted.

17. A wound dressing comprising:
- a transparent breathable film covering an entire outer surface of the wound dressing;
- a transparent fluid-wicking layer that is continuous and completely overlays the transparent breathable film; and
- a fluid-absorption layer positioned between the transparent breathable film and the transparent fluid-wicking layer;
- wherein the transparent fluid-wicking layer directs fluid towards the fluid-absorption layer; and
- wherein the wound dressing comprises a transparent part that enables observation of a wound, the fluid-absorption layer being a continuous layer that encloses the transparent part.

* * * * *